United States Patent [19]

Hargens et al.

[11] 4,192,319
[45] Mar. 11, 1980

[54] WICK CATHETER PRESSURE SENSING PROBE AND METHOD OF USE

[75] Inventors: Alan R. Hargens; Scott J. Mubarak, both of San Diego, Calif.

[73] Assignee: Regents of University of California, Berkeley, Calif.

[21] Appl. No.: 838,187

[22] Filed: Sep. 30, 1977

[51] Int. Cl.$^2$ .......................... A61B 5/02; A61M 5/00
[52] U.S. Cl. .................................. 128/748; 128/673; 128/214.4
[58] Field of Search ................ 128/2.05 D, 214.4, 348

[56] References Cited

U.S. PATENT DOCUMENTS

| | | | |
|---|---|---|---|
| 2,426,535 | 8/1947 | Turkel | 128/2 B |
| 2,847,990 | 8/1958 | Ayre | 128/2 B |
| 3,570,485 | 3/1971 | Reilly | 128/214.4 |
| 3,739,778 | 6/1973 | Monestere et al. | 128/214.4 |

OTHER PUBLICATIONS

"Biopsy Needles & Instruments for Advanced Techniques," pub. by Becton, Dickinson & Co., (#1471, Sternal Bone Marrow Infusion Needle, Trephine type). "The Lancet," Oct., 1964, pp. 941-942—article on "Diagnostic Right-Heart Catheterization with Miniature Catheters. . . ."

Primary Examiner—Robert W. Michell
Assistant Examiner—C. W. Shedd
Attorney, Agent, or Firm—Jessup & Beecher

[57] ABSTRACT

This invention relates to a clinical wick catheter and to a technique for measuring tissue fluid pressure and also collecting tissue fluid by the catheter.

A catheter tube has a wick positioned in one end which is drawn into place by a monofilament tether extending through the catheter tube. In use, a sheathed placement needle is first partially inserted beneath the skin and fascia of the subject patient; the needle is partially retracted into the sheath; the assembly is then further inserted into the muscle tissue of interest. The needle is then withdrawn and replaced by the catheter which is inserted, wick first, through the sheath until the wick resides in the tissue region of interest. Thereafter, the interstitial fluids soak into the wick and the pressure transmitted through the catheter via the medium of a saline solution which fills the catheter. The outer end of the catheter is connected to pressure (negative or positive) measuring equipment, such as a manometer.

7 Claims, 9 Drawing Figures

WICK CATHETER PRESSURE SENSING PROBE AND METHOD OF USE

SUMMARY OF THE INVENTION

It is known, e.g, Scholander, et al, Negative Pressure in the Interstitial Fluid of Animals, Science, 161:321-328, 7-26-68, to insert a catheter carrying a wick at the end in order to measure the interstitial pressure. The Scholander wick consists of a piece of loose cotton pulled into the end of the catheter tubing by means of a loop which is removed once the wick is in position. The present invention employs a wick consisting of two short lengths of multifilament, substantially uniform, synthetic plastic braid, doubled back on itself, with the bight drawn into the intratissue end of the catheter. The braid wick is drawn into the catheter by means of a monofilament tether having one end tied securely to the bight of the wick, the tether then extending through the catheter to the other end of the tube. The tether is left in place after the wick is positioned so that should the wick work itself loose, it may be retrieved by virtue of its fixed securement to the tether, the outer end of the tether being readily accessible at the outer end of the catheter.

The present invention also contemplates a method of inserting the catheter into a desired interstitial region within the tissue, with minimal tissue damage and edema.

A preferred form of the present invention, both apparatus and method, will now be described with reference to the accompanying drawings wherein:

DETAILED DESCRIPTION OF THE PREFERRED EMBODIMENT

Figure 1A:
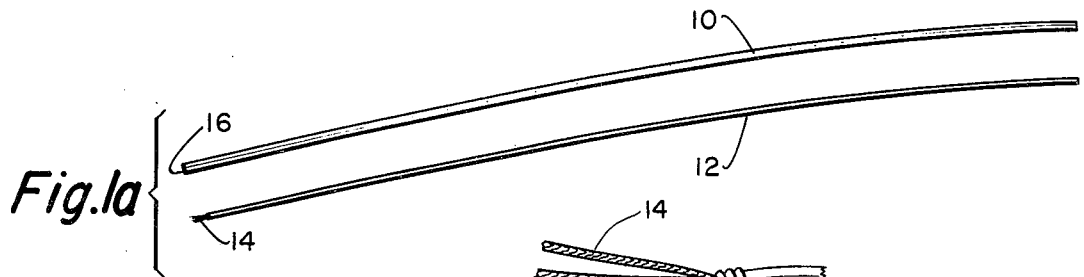
FIG. 1a illustrates a catheter tube, and a monofilament tether with a braided wick at the end, which is adapted to be drawn into the tube prior to use.
Figure 1B:
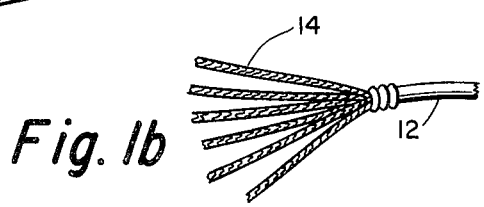
FIG. 1b is a detail view to show the braided wick at the end of the tether.

Referring to FIG. 1, 10 is an epidural catheter with a length, for example, of 20 cm, an outside diameter of 1.02 mm, and an inside diameter of 0.62 mm. Numeral 12 is a nylon or polypropylene monofilament tether having a uniform diameter of approximately 80–100 micrometers i.e., microns and a length of approximately 25 cm. The left end of the tether 12 is tied to the midpoint or bight of a wick 14 made of soluble braided polyglycolic acid suture having a uniform fiber diameter of approximately 20 micrometers. Typically, two parallel braided lengths, each approximately 2.5 cm long, may be tied at their common bights to the nylon monofilament 12.

Figure 3:
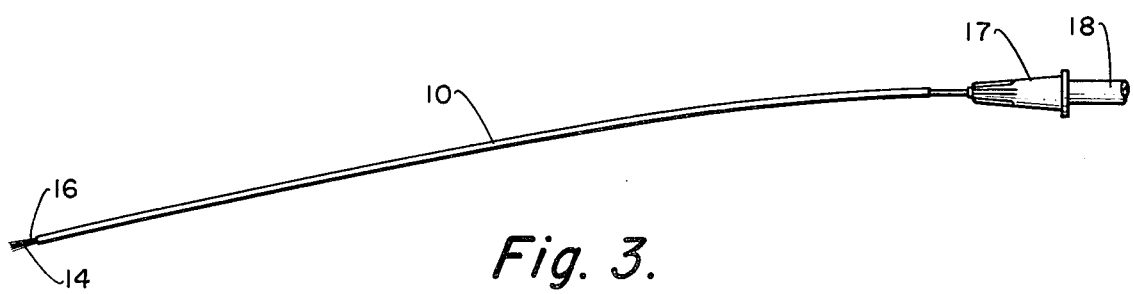
FIG. 3 is a further view of the catheter showing schematically the attachment of the adapter to a capillary tube which transmits the pressure to a manometer or pressure transducer.

The right end of the monofilament 12 is passed from left to right through the catheter 12 and the wick 14 is drawn approximately half of its length into the left end 16 of the catheter 10, leaving approximately 0.6 cm of the wick outside the end 16 of the catheter tube 10. The catheter tube is then fitted with an adapter 17 so that it may be connected to suitable pressure measuring equipment. This is shown in FIG. 3, where the tube 18 fitted to the outer end of the adapter 17 may lead to a manometer or transducer for measuring interstitial pressure as detected by the fluids picked up through microchannels of the wick 14. A suitable pressure measuring technique is disclosed in the aforementioned Scholander article.

At an expedient point in this procedure, the catheter 10, adapter 17, and tubing 18 are filled with sterile heparinized saline solution to transmit fluid pressure built up in the wick, and the pressure measuring equipment is calibrated. The catheter is now ready for insertion into the body of the patient.

Figure 2:
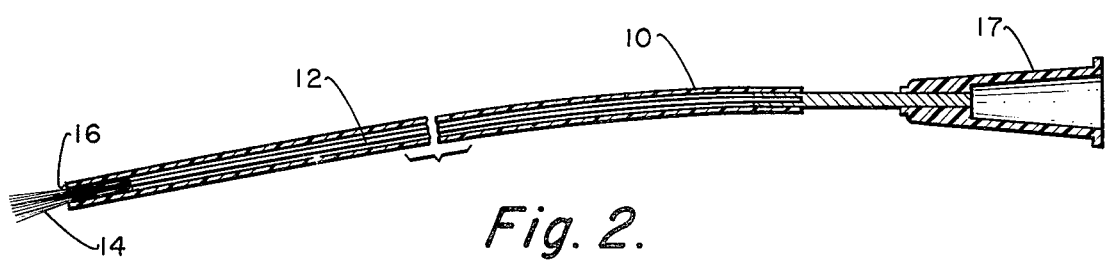
FIG. 2 illustrates the tether and wick in position inside the catheter tube. The outer end of the catheter is fitted with a standard adapter for conventional, clinical and hospital pressure measuring apparatus.
Figure 4:
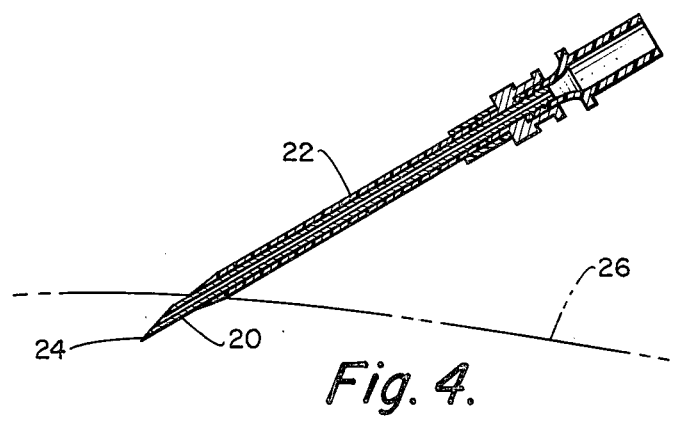
FIG. 4 illustrates a first step in the process or method of inserting the wick into the desired tissue region.
Figure 5:
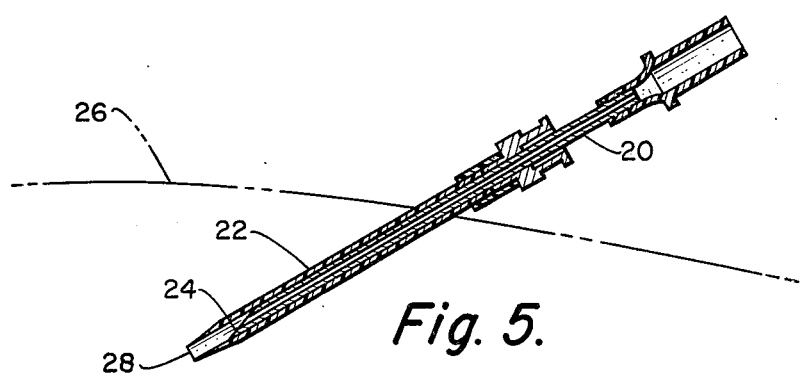
FIG. 5 illustrates a second step in the insertion process.
Figure 6:
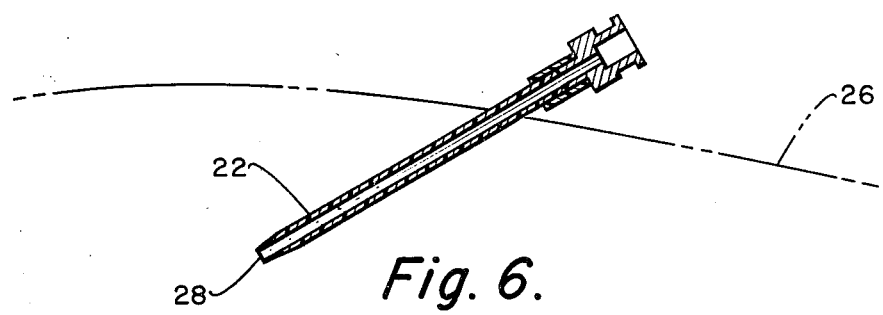
FIG. 6 illustrates a third step in the insertion process.
Figure 7:
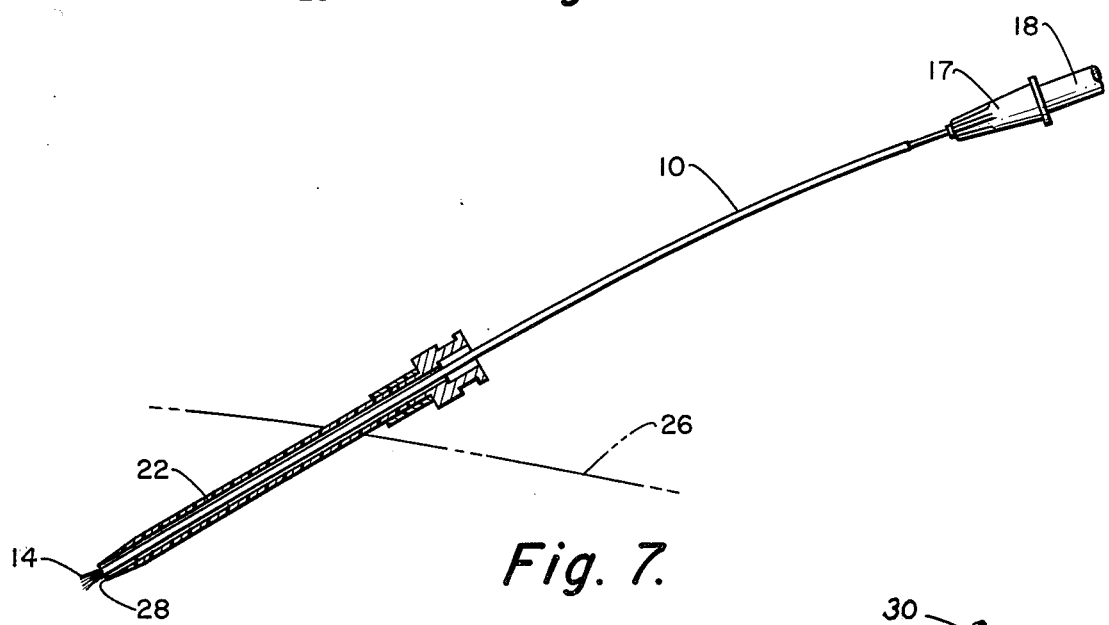
FIG. 7 illustrates the next step, showing the catheter tube inserted through the sheath. In the final position of the parts (not shown) the sheath is removed from the body and slid back along the catheter tube.

This is accomplished by apparatus and method shown in FIGS. 4 through 7. FIG. 4 illustrates a metal catheter placement needle 20 sheathed by a plastic sheath 22, with the pentrating point 24 of the needle 20 extending slightly beyond the sheath 22. With the parts positioned as shown in FIG. 4, the assembly is inserted through the skin 26 of the patient and through the outer layer of subcutaneous tissue (fascia) which is typically of relatively high penetration resistance. After this high-resistance tissue has been penetrated, the needle 20 is partially retracted within the sheath 22, as shown in FIG. 5, so that the tip 24 of the needle 20 lies within the end of the sheath 22, leaving the tip 26 of the sheath 22 to serve as the penetrating point for further and deeper tissue insertion. The plastic sheath or tubing 22, being of softer material, is appreciably less damaging to the internal tissue as it proceeds inward, than is the metal point 24. Because of the easier penetration, it is able to satisfactorily penetrate further into a desired placement region inside the tissue. During this second phase of the insertion, the metal needle 22 remains in position to rigidify the sheath 22. When the tip 26 of the sheath 22 has been inserted to a point of desired placement, the metal needle 20 is completely withdrawn from the sheath 22 and laid aside, as shown in FIG. 6. Thereafter, the catheter, with tether and wick, as shown in FIG. 2, is inserted through the sheath 22, wick first, until the wick 14 clears the end 26 of the sheath 22 and resides at the desired placement region, as shown in FIG. 7. The operator or technician senses this placement by the fact that resistance to further insertion of the catheter 10 is encountered when the wick 14 clears the end 26 of the sheath 22.

To ascertain that the apparatus is correctly inserted and positioned, the doctor presses inward or squeezes at the region where the measurement is desired. This should produce a marked transient excursion in the manometer reading. If it does not, then the wick should be cleared by flushing with a small amount of saline solution.

After placement of the catheter 10, the sheath 22 is pulled out of the body and slid along the catheter 10 out of the way. The apparatus is then ready to make interstitial pressure measurements in accordance with known techniques as taught, for example, in Scholander.

The wick is removed by pulling out the catheter slowly until the tip has cleared the skin. If the wick has slipped out, it may be easily retrieved by the tether 12.

Figure 8:
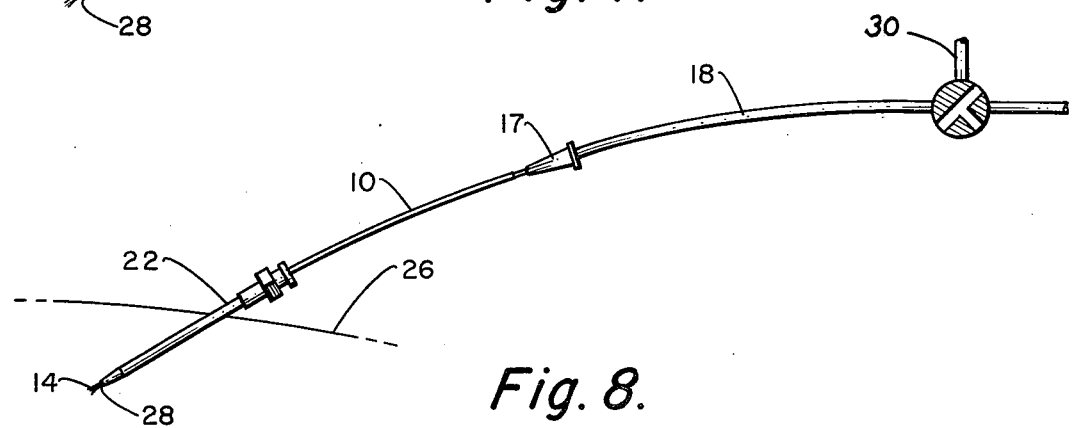
FIG. 8 is a schematic view corresponding to FIG. 7, illustrating an alternative use of the apparatus for withdrawing interstitial fluid from a desired tissue region.

In addition to being useful for measuring interstitial fluid pressure, the present apparatus and method are also readily adaptable for the withdrawal of interstitial fluids. In this case, the same apparatus and techniques are employed except that the catheter is left empty instead of being filled with saline solution. Thus, when the wick 14 is in position in the desired interstitial tissue region, the capillary action of the wick 14 draws tissue fluids into the end of the catheter 10 and then into the bore of the catheter 10. In the case of edema, the fluid pressure within the tissue itself is usually enough to drive a sufficient amount of tissue fluid into the catheter, which may then be pulled from the muscle or other tissue, and the fluid removed for appropriate examination. If desired, a vacuum may be applied at 30 to the exterior end of the catheter, as shown in FIG. 8, to further amplify the withdrawal of fluid from the tissue via the wick 14 into the catheter 10.

For a further understanding of the clinical implications of the present invention, as well as a bibliography of additional references, reference is made to (1) Mubarak, et al., "The Wick Catheter Technique for Measurement of Intramuscular Pressure", The Journal of Bone and Joint Surgery, Volume 58-A, No. 7, pages 1016–1020, October 1976, and (2) Hargens, et al., "Interstitial Fluid Pressure on Muscle and Compartment Syndromes in Man", Microvascular Research, Volume 14, pages 1–10, October 1977.

What is claimed is:

1. A method of measuring interstitial pressures comprising:
    inserting a sheathed placement needle through the skin and through any other region of relatively high penetration resistance;
    partially withdrawing the needle into the sheath so that the tip of the needle is within the sheath;
    further inserting the sheath and needle to a desired placement within a tissue of interest;
    withdrawing the needle, leaving the sheath in place;
    attaching a tether to a wick;
    positioning the wick partially in one end of a catheter which has an adapter attached to its other end;
    filling the catheter with a sterilized heparinized solution;
    inserting the catheter tube with wick into the sheath until the one end thereof resides at the desired placement within the body tissue;
    connecting a pressure-sensing and indicating means to the adapter on said other end.

2. The method according to claim 1 wherein the step of attaching the tether comprises:
    attaching a length of monofilament to a wick of substantially uniform synthetic plastic braid doubled on itself with said monofilament tied to the bight of said braid.

3. The method according to claim 1 or 2 wherein the step of positioning the wick comprises:
    drawing the tether through the tube until the wick is drawn partially into the tube.

4. The method according to claim 1 wherein the step of inserting the sheathed placement needle comprises:
    inserting a sheathed placement needle wherein the sheath is of a softer material than the needle.

5. A catheter unit for placement and measuring of interstitial pressures comprising:
    a catheter tube;
    an adapter on one end of said tube;
    a wick partially drawn into the other end of said tube;
    a monofilament tether having one end fixedly secured to said wick, said tether extending through said tube with the other end of said tether adjacent to said one end of said tube;
    said tube being filled with a sterilized heparinized solution; and
    pressure-sensing and indicating means connected to said adapter whereby interstitial pressure may be measured after insertion of the catheter tube and wick to the desired placement within the body tissue.

6. The catheter unit according to claim 5 wherein said wick comprises a substantially uniform synthetic plastic braid doubled on itself to form a bight.

7. The catheter unit according to claim 6 wherein said tether is tied to said bight for drawing said wick partially into said other end of said tube.

* * * * *